US008550987B2

(12) United States Patent
Abe

(10) Patent No.: US 8,550,987 B2
(45) Date of Patent: Oct. 8, 2013

(54) ELECTRONIC ENDOSCOPE APPARATUS

(75) Inventor: Kazunori Abe, Saitama (JP)

(73) Assignee: FUJIFILM Corporation, Tokyo (JP)

(*) Notice: Subject to any disclaimer, the term of this patent is extended or adjusted under 35 U.S.C. 154(b) by 677 days.

(21) Appl. No.: 12/411,970

(22) Filed: Mar. 26, 2009

(65) Prior Publication Data
US 2009/0244271 A1 Oct. 1, 2009

(30) Foreign Application Priority Data

Mar. 27, 2008 (JP) ................. 2008-084405

(51) Int. Cl.
A61B 1/00 (2006.01)
(52) U.S. Cl.
USPC ........................................................ 600/118
(58) Field of Classification Search
USPC ........................................................ 600/118
See application file for complete search history.

(56) References Cited

U.S. PATENT DOCUMENTS

| 6,322,496 B1* | 11/2001 | Iida et al. | 600/118 |
| 2004/0036899 A1* | 2/2004 | Takano et al. | 358/1.9 |
| 2006/0155166 A1* | 7/2006 | Takahashi et al. | 600/109 |
| 2007/0100202 A1* | 5/2007 | Murata | 600/109 |
| 2007/0167673 A1* | 7/2007 | Enomoto | 600/101 |

FOREIGN PATENT DOCUMENTS

| JP | 7-116115 A | 5/1995 |
| JP | 9-276214 A | 10/1997 |
| JP | 2000-60789 A | 2/2000 |

OTHER PUBLICATIONS

Japanese Office Action dated Jun. 26, 2012 was issued in corresponding Japanese Application No. JP 2008-084405.

* cited by examiner

Primary Examiner — Hieu Hoang
(74) Attorney, Agent, or Firm — Birch, Stewart, Kolasch & Birch, LLP

(57) ABSTRACT

An electronic endoscope apparatus having a scope and a processor. The processor includes a plurality of image processing means and a first setting means. Each of the image processing means performs different image processing. ON/OFF of functions and/or parameters used for the processing are set individually with respect to each of the image processing means. The scope includes a memory having at least one area configured to store ON/OFF setting of the function of each of the image processing means and/or a value of the processing parameter used for each processing. The first setting means of the processor reads information stored in the area of the memory of the scope to set the function of each of the image processing means to ON or OFF and supply a predetermined parameter to each of the image processing means based on the information.

3 Claims, 5 Drawing Sheets

FIG.4

FUNCTION SETTING SCREEN (SCOPE)

1. HYPER-TONE       OFF   Low   Mid   High
2. SHARPNESS        OFF   Low   Mid   High
3. COLOR ENHANCEMENT OFF  Low   Mid   High
4. NOISE REDUCTION  OFF   Low   Mid   High
5. LIMITED FREQUENCY OFF  ON
6. FREQUENCY        0
7. SAVE SETTING     YES   NO

INPUT AREA NUMBER [ ]

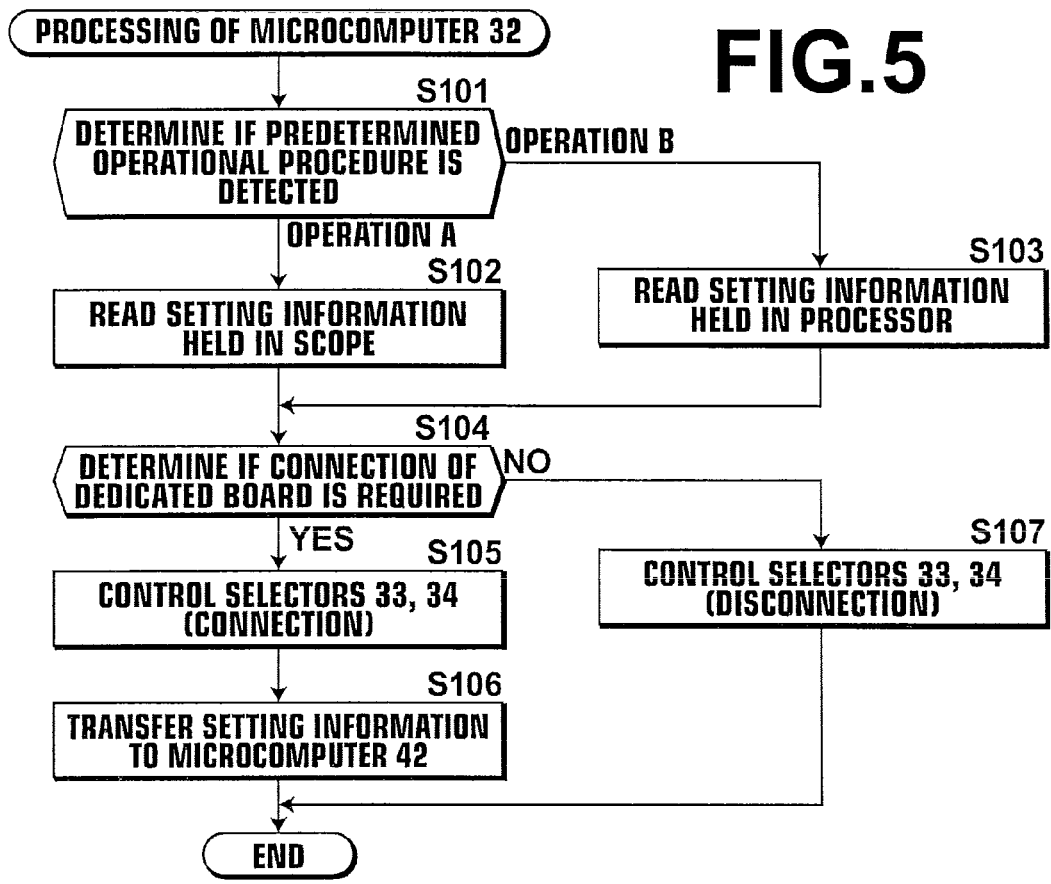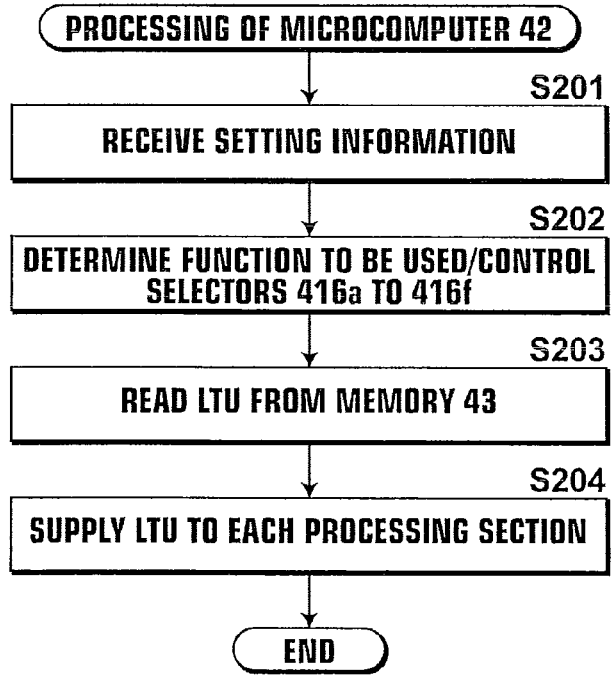

ELECTRONIC ENDOSCOPE APPARATUS

BACKGROUND OF THE INVENTION

1. Field of the Invention

The present invention relates to function-selection and parameter setting for an electronic endoscope apparatus having a plurality of different image processing functions.

2. Description of the Related Art

Generally, an electronic endoscope apparatus has a plurality of different image processing functions, such as color adjustment function, shade adjustment function, sharpness adjustment function, noise reduction function, and the like. These types of image processing are performed in the main body (processor) of the electronic endoscope apparatus. A user of the electronic endoscope apparatus sets ON/OFF of each image processing function and a parameter required for each processing on the processor in order to make a diagnostic image displayed on the monitor appear desirable.

The setting contents, in most cases, are basically identical if the inspection object or purpose is the same. Consequently, most electronic endoscope apparatuses are configured such that a set of setting results of each function is stored in a memory of the processor so as to be reused at a later time as described, for example, in Japanese Unexamined Patent Publication Nos. 9(1997)-276214 and 7(1995)-116115.

But even where the inspection object or purpose is the same, recommended settings may differ from hospital to hospital. In addition, appropriateness of the displayed image also depends on the experience or preference of the doctor who performs the diagnosis. Therefore, even where the inspection object or purpose is the same, desirable settings may differ from doctor to doctor. Consequently, doctors who do not always perform inspections at the same place, such as those who work for a plurality of hospitals, need to set ON/OFF of each function and a processing parameter for each function every time before performing an inspection. For a multifunctional apparatus, in particular, there are many items to be set which causes a problem that it requires a fair amount of preparation time for inspection. It is an object of the present invention, therefore, to reduce the burden of such setting work prior to inspection.

SUMMARY OF THE INVENTION

An electronic endoscope apparatus of the present invention includes a scope and a processor for processing an image obtained by the scope.

The processor includes a plurality of image processing means, each for performing a different type of image processing on the image, configured such that ON/OFF of functions thereof and/or processing parameters therefor are set individually with respect to each of the image processing means. The plurality of image processing means includes, for example, a color adjustment means, a brightness adjustment means, a sharpness enhancement means, a noise reduction means, and the like. The processor further includes a first setting means for setting a function of each of the image processing means to ON or OFF and supplying a predetermined parameter to each of the image processing means. In the mean time, the scope includes a memory having at least one area configured to store ON/OFF setting of the function of each of the image processing means and/or a value of the processing parameter used by each of the image processing means. In this configuration, the first setting means of the processor reads information stored in the area of the memory of the scope and performs the setting of each of the functions based on the information.

In the configuration described above, setting information of each of the functions of the processor is held in the scope, and each of the functions of the processor is set automatically based on the setting information read out from the memory of the scope. Therefore, a doctor may carry around a scope with desired setting information stored therein and connect the scope to a processor provided on the site where an inspection takes place, whereby the electronic endoscope system to be used for the inspection can be set to desired conditions instantaneously.

Preferably, the processor further includes an input means for accepting input of ON/OFF of the functions and/or the processing parameters individually with respect to each of the image processing means, and a second setting means configured to store ON/OFF setting of the function and/or the processing parameter specified through the input means with respect to each image processing means in the memory of the scope. This eliminates the need for providing an input means for storing setting information on the scope side. Consequently, addition of the functions described above does not require the structure of a scope to be changed.

Preferably, the memory of the scope has the area in a plurality. This allows ON/OFF settings of the functions and values of the processing parameters to be stored with respect to each inspection object or inspection purpose. Further, where the same scope is shared by a plurality of doctors, ON/OFF settings of the functions and values of the processing parameters may be stored individually with respect to each of the doctors.

Preferably, information is read out from the memory of the scope when a predetermined operational procedure is performed on the electronic endoscope apparatus. This allows a doctor to select whether to use the own setting information stored in the scope or setting information stored in the processor, otherwise newly set depending on the situation.

BRIEF DESCRIPTION OF THE DRAWINGS

FIG. 4 illustrates an example setting screen.

FIG. 5 is a flowchart illustrating the processing of microcomputer 32.

FIG. 6 is a flowchart illustrating the processing of microcomputer 42.

DESCRIPTION OF THE PREFERRED EMBODIMENTS

Hereinafter, an electronic endoscope system used for inspecting a digestive organ will be described as an embodiment of the present invention.

Figure 1:
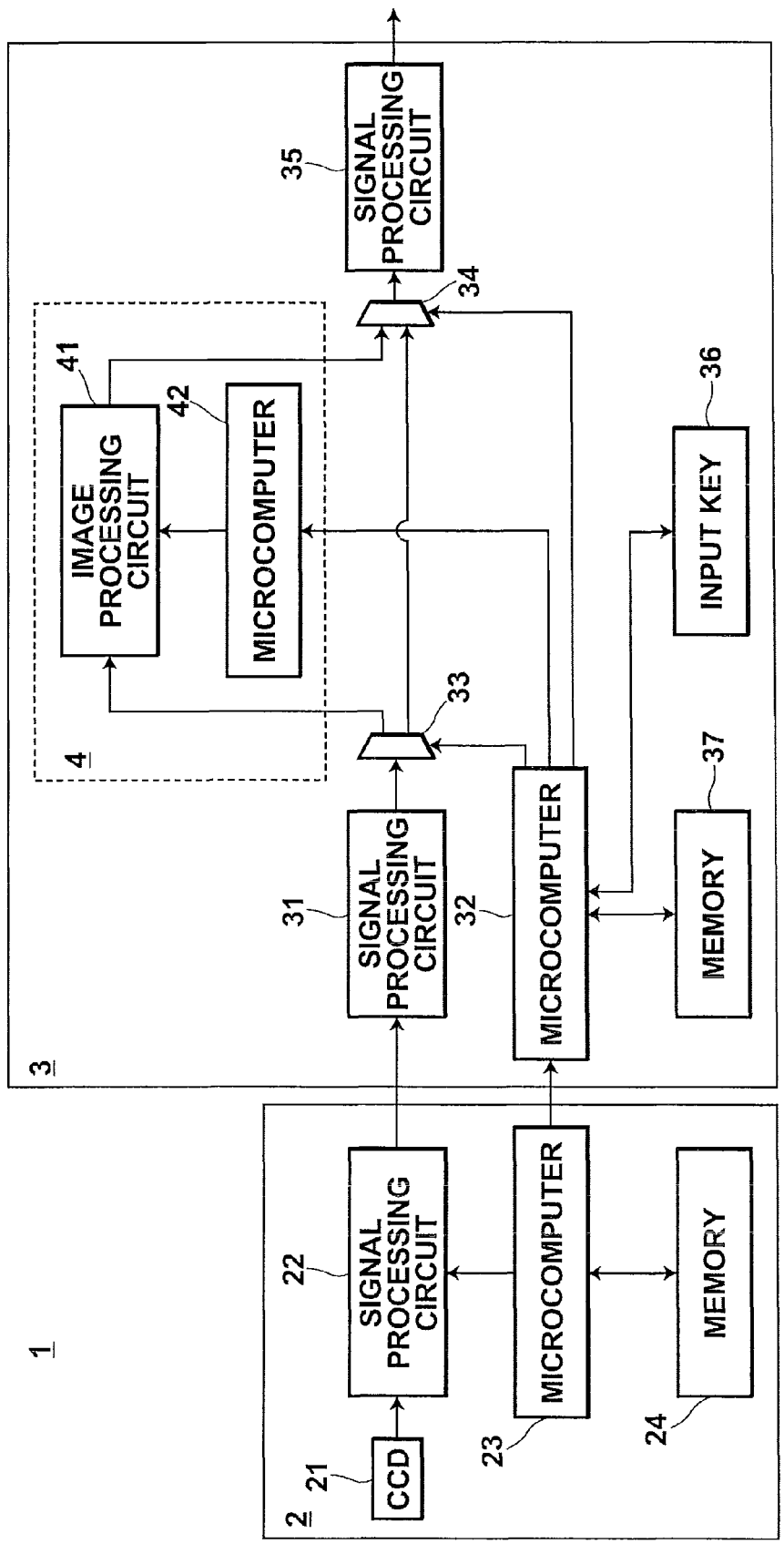
FIG. 1 is a diagram of an electronic endoscope system, illustrating the schematic configuration thereof.

FIG. 1 is a diagram of the electronic endoscope system, illustrating the schematic configuration thereof. As illustrated in FIG. 1, electronic endoscope system 1 includes electronic endoscope 2 (hereinafter, scope 2), processing unit 3 (hereinafter, processor 3) for processing an image obtained by scope 2, a not shown light source unit, a monitor, a printer, and the like. Electronic endoscope system 1 allows the use of a plurality of different scopes according to the purpose of the inspection, scope 2 shown in FIG. 1 represents the configuration common to these scopes.

Scope 2 includes CCD (Charge Coupled Device) 21, signal processing circuit 22 for processing a signal obtained by CCD 21, microcomputer 23 for performing various controls, memory 24, and a not shown connector unit to be connected to processor 3.

CCD 21 is attached to the distal end of scope 2, together with an objective lens. CCD 21 obtains reflection light from an observation object and converts the light to an electrical signal. In the present embodiment, the imaging resolution of the CCD is about 5 µm. Signal processing circuit 22 performs signal processing, such as correlated double sampling, automatic gain control, A/D conversion, on the output signal of CCD 21. Microcomputer 23 controls the operation of the signal processing circuit and data transfer to processor 3.

Memory 24 has a plurality of setting information storage areas. Each setting information storage area may store ON/OFF setting values of all of the functions of processor 3 and processing parameters. In the present invention, default setting information set by the manufacturer is stored in the leading storage area.

Figure 2:
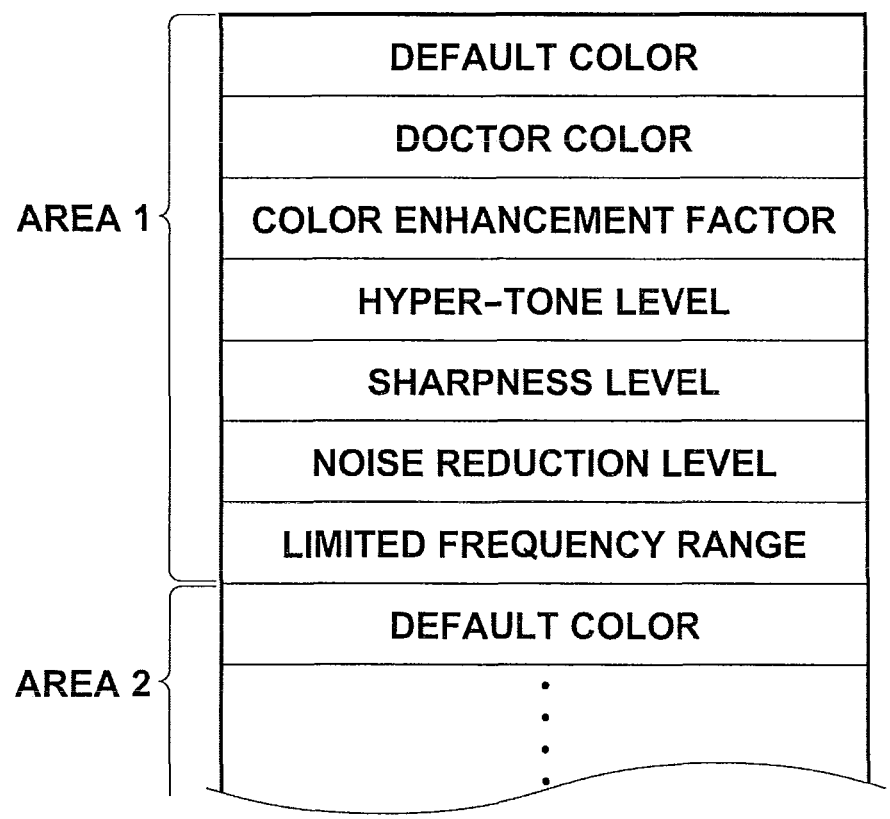
FIG. 2 illustrates setting information storage areas of a memory.

FIG. 2 illustrates example setting information storage areas of memory 24. As shown in FIG. 2, each setting information storage area includes default color, doctor color, color enhancement factor, hyper-tone level, sharpness level, noise reduction level, and identifier for identifying limited frequency range.

The default color includes a default color value set by the manufacturer at the time when the scope is shipped, which is set for each of R, G, and B. The doctor color includes a default color value of the owner or a user of the scope, which is also set for each of R, G, and B. These color values are set by the doctor who routinely uses the scope by performing a predetermined operational procedure.

The color enhancement factor is a parameter indicating the enhancement level of a predetermined color, and the value corresponding to a color value set as the default value or doctor value multiplied by the color enhancement factor becomes the color value when displayed on the monitor. When the color enhancement factor is set to "0", the color enhancement function is disabled.

The hyper-tone level is a parameter indicating the brightness adjustment level. Hyper-tone processing is processing for converting only a brightness value in a dark region to a higher brightness value while maintaining a brightness value in a bright region as it is. In the present embodiment, conversion level of the brightness value may be changed in three steps according to the setting value of the hyper-tone level. When the hyper-tone level is set to "0", the hyper-tone processing function is disabled.

The sharpness level is a parameter indicating the sharpness enhancement level. In the present embodiment, the sharpness level may be changed in three steps according to the setting value of the sharpness level. When the sharpness level is set to "0", the sharpness enhancement function is disabled. The noise reduction level is a parameter specifying the noise reduction level. When the noise reduction level is set to "0", the noise reduction function is disabled.

The identifier for identifying a limited frequency range is a number or another identifier identifying a predetermined frequency range. The relationship between the frequency range and identifier is stored in memories of scope 2 and processor 3 in advance. The electronic endoscope system of the present embodiment has a function to improve visualization of a particular structure (e.g., blood vessel) by enhancing frequency signals within a predetermined range included the image. The setting of limited frequency range is a setting related to this function.

Now, returning to FIG. 1, the configuration of processor 3 will be described. Processor 3 includes a not shown connector unit. The connector unit of processor 3 has a structure that allows easy connection or disconnection of the connector of each scope described above.

Processor 3 includes signal processing circuit 31 that performs gamma correction on a signal inputted via the connector unit and generates a video signal. When the output signal of signal processing circuit 22 of the scope is a CMYG signal, signal processing circuit 31 also performs conversion of the CMYG signal to an RGB signal. Processor 3 further includes microcomputer 32 that controls operation of signal processing circuit 31 and communication with scope 2. Signal processing circuit 35 that generates a monitor output signal by performing pixel number conversion and D/A conversion is disposed in the latter stage of signal processing circuit 31.

Processor 3 further includes memory 37 having a plurality of setting information storage areas. Memory 37 may store setting information identical to that stored in memory 24 of scope 2. In the present embodiment, default setting information set by the manufacturer is stored in the leading storage area.

Processor 3 further includes input key 36 for inputting a character or a numerical value to microcomputer 32 from the outside. Input key 36 may be a keyboard built-in the body of processor 3 or a keyboard externally attached to processor 3.

Processor 3 further includes dedicated image processing board 4 in addition to a main board on which signal processing circuit 31, microcomputer 32, and signal processing circuit 35 are mounted. Mounted on dedicated image processing board 4 are image processing circuit 41 that performs various types of image processing on an image signal outputted from signal processing circuit 31, and microcomputer 42 that controls image processing circuit 41. Image processing circuit 41 is connected to signal processing circuits 31 and 35 via selectors 33 and 34 respectively. Selectors 33 and 34 are switched based on control signals from microcomputer 32.

Figure 3:
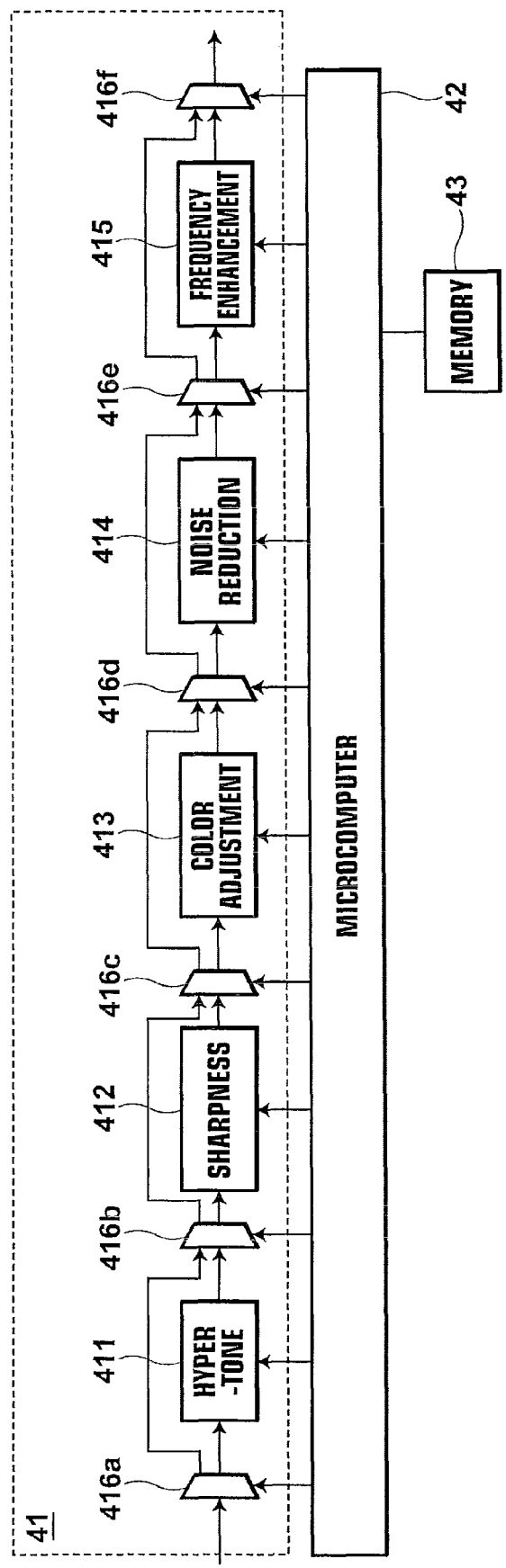
FIG. 3 is a diagram of a dedicated image processing board, illustrating the detailed configuration thereof.

The detailed configuration of dedicated image processing board 4 is shown in FIG. 3. As shown in FIG. 3, image processing circuit 41 is divided into five processing sections: hyper-tone processing section 411, sharpness processing section 412, color adjustment section 413, noise reduction processing section 414, and frequency enhancement processing section 415. Each of processing sections 411 to 415 can be selectively operated by switching selectors 416a to 416f. That is, ON/OFF of each processing function can be set individually. Selectors 416a to 416f are switched based on control signals supplied from microcomputer 42. Memory 43 is also mounted on dedicated image processing board 4. Memory 43 has stored therein lookup tables used by hyper-tone processing section 411, sharpness processing section 412, and color adjustment section 413, and the like. Microcomputer 42 supplies a lookup table required by each processing section according to the setting.

Storage of setting information in memory 24 of scope 2 and storage of setting information in memory 37 of processor 3 may be performed on a setting screen displayed on an operation panel (or on the monitor connected to processor 3). An example setting screen for storing setting information in memory 24 of scope 2 is shown in FIG. 4. Items 1 to 5 displayed on the setting screen correspond to hyper-tone processing section 411, sharpness processing section 412, color adjustment section 413, noise reduction processing section 414, and frequency enhancement processing section 415 respectively, and ON/OFF setting of each processing function and levels when each function is set to ON are displayed as the selection options. Item 6 is an item to be set only when ON is selected in item 5, in which entry of a number allows the frequency range related to the number to be selected. Shifting from one displayed item to another, and selection of item are implemented using input key 36. After selection for each of items 1 to 6 is completed, if "YES" is selected in item 7, a message inquiring the storage area number is outputted, as shown in FIG. 4. When a number specifying the storage area is inputted and Enter Key is depressed, a message prompting final confirmation (not shown) is outputted, and if Enter Key is depressed again, the setting information is stored in the storage area of memory 24 corresponding to the specified number.

The display of the setting screen is controlled by microcomputer 32. Microcomputer 32 accepts selection input from input key 36, and transfers the number identifying the storage area and values selected for items 1 to 6 to microcomputer 23 of scope 2. The setting information is stored in memory 24 by microcomputer 23 that has received the information.

The setting screen for storing setting information in memory 37 of processor 3 is basically the same as that shown in FIG. 4. If "YES" is selected in item 7, however, a message inquiring the number of the storage area in memory 37 of processor 3 is outputted. In addition, the specified number and values selected for items 1 to 6 are stored in memory 37 by microcomputer 32 itself.

The operation of processor 3 when endoscopic inspection is performed by connecting scope 2, with setting information stored therein, to processor 3 will be described. When power is supplied to processor 3, microcomputer 32 performs the steps of communicating with microcomputer 23 of scope 2 to verify the connection between them, reading default setting information from the leading storage area of memory 37, controlling selectors 33 and 34 based on the default setting information, and supplying the setting information to microcomputer 42.

FIG. 5 is a flowchart illustrating the processing performed by microcomputer 32 when setting processor 3 based on the stored setting information. When a predetermined operational procedure is performed by a user, the operational instruction is detected by microcomputer 32 (S101). If the detected instruction is an instruction to read the setting information stored in scope 2, microcomputer 32 requests microcomputer 23 to transfer the setting information stored in memory 24. If the detected instruction is an instruction also including specification of storage area, microcomputer 32 requests microcomputer 23 to transfer only the setting information stored in the specified storage area. While if the detected instruction is an instruction that does not include specification of storage area, microcomputer 32 requests microcomputer 23 to transfer setting information stored in all of the storage areas, and displays a selection screen for having a user to select storage area on the monitor or the like. If setting information is stored in the storage area specified by microcomputer 32, microcomputer 23 transfers the setting information to microcomputer 32. This results in that the setting information held in scope 2 is read into microcomputer 32 (S102).

If setting information is not stored in the storage area specified by microcomputer 32, microcomputer 23 sends an error notification signal to microcomputer 32. When the error notification signal is received, microcomputer 32 outputs a message indicating that setting information is not stored in the specified storage area.

In the mean time, if the detected instruction is an instruction to read setting information stored in processor 3, microcomputer 32 directly accesses memory 37. This results in that the setting information held by processor 3 is read into microcomputer 32 (S103).

After the setting information is read in, microcomputer 32 determines if it is necessary to establish connection with dedicated image processing board 4 (S104). More specifically, microcomputer 32 refers to the values of color enhancement factor, hyper-tone level, sharpness level, noise reduction level, and limited frequency range of the setting information, and if all of the values are set to "0", microcomputer 32 determines that the connection with dedicated image processing board 4 is not required, while it determines that the connection with dedicated image processing board 4 is required if any one of the items is set to a value other than "0".

When a determination is made that the connection with dedicated image processing board 4 is required, microcomputer 32 controls selector 33 and selector 34 so that signal processing circuit 31 and signal processing circuit 35 are connected to dedicated image processing board 4 (S105). Then, microcomputer 32 transfers the setting values of doctor color and setting values of color enhancement factor, hyper-tone level, sharpness level, noise reduction level, and limited frequency range to microcomputer 42 of dedicated image processing board 4 (S106).

On the other hand, when a determination is made that the connection with dedicated image processing board 4 is not required, microcomputer 32 controls selector 33 and selector 34 so that signal processing circuit 31 and signal processing circuit 35 are disconnected from dedicated image processing board 4, that is, output of signal processing circuit 31 is directly inputted to signal processing circuit 35 (S107).

FIG. 6 is a flowchart illustrating the processing performed by microcomputer 42 that receives the setting information transferred in step S106. When the setting information transferred from microcomputer 32 is received (S201), microcomputer 42 determines a function to be used, and controls selectors 416a to 416f so that only the processing section involved in the function is operated (S202). The function to be used is determined by determining whether or not each of the setting values of color enhancement factor, hyper-tone level, sharpness level, noise reduction level, and limited frequency range is "0". For example, when the value of sharpness level is set to "0", it indicates that the sharpness processing section is set to OFF. Therefore, microcomputer 42 controls selector 416b and selector 416c so that output of hyper-tone processing section 411 is directly inputted to color adjustment section 413.

If the processing section to be operated performs processing using a lookup table, microcomputer 42 loads the lookup table stored in memory 43 (S203). The lookup table is selected based on the setting information. For example, the lookup table used by hyper-tone processing section 411 for brightness value conversion differs depending on the specified level. Therefore, microcomputer 42 reads the appropriate lookup table selected according to the specified level from memory 43. Then, microcomputer 42 supplies a required lookup table to each of the processing sections whose functions are set to ON (S203).

In the present embodiment described above, parameters indicating whether each of processing sections 411 to 415 of dedicated image processing board 4 is set to ON or OFF, processing level performed by each of processing section 411 to 414, and frequency range limited by processing section 415 are stored not only in memory 37 of processor 3 but also in memory 24 of scope 2. Then, when a predetermined operational procedure is performed by a doctor, the setting information stored in memory 24 of scope 2 is read into processor 3, and each processing section of dedicated image processing board 4 is set automatically. Consequently, a doctor may carry around a scope with desired setting information stored therein and connect the scope to a processor provided on the site where an inspection takes place, whereby the electronic endoscope system to be used for the inspection can be set to desired conditions instantaneously.

Further, in the present embodiment described above, the setting information is stored in scope 2 by connecting scope 2 to processor 3 and using the display/input function of processor 3. This eliminates the need for providing a particular device for storing setting information on the side of scope 2, and setting information may be stored in scope 2 in the same procedure as that when storing setting information in processor 3. In the present embodiment described above, microcomputer 32 has both functions of the first and second setting means of the present invention. But a setting means for storing setting information in scope 2 may be provided separately from microcomputer 32. Further, as an alternative embodiment, a configuration may be conceivable in which a simple input/setting means is provided on the side of scope 2.

Still further, in the present embodiment described above, memory 24 of scope 2 has a plurality of setting information storage areas, so that a plurality of different sets of setting information, each for each inspection object or inspection purpose, may be stored in scope 2. Further, even where one scope is shared by a plurality of doctors, each doctor may store desired setting information in the scope, since doctor color is provided, as one type of setting information. But, a plurality of setting information storage areas is not necessarily required and one storage area may be satisfactory.

Further, in the present embodiment described above, setting information is also stored in processor 3, as in a conventional system, and setting information stored in scope 2 is read into processor 3 only when a predetermined operational procedure is performed. Therefore, a doctor may select whether to use the own setting information stored in the scope or setting information stored in the processor, otherwise newly input setting information depending on the situation. But, a configuration may be adopted in which a memory is not provided in a processor and setting information is stored only in a scope.

What is claimed is:

1. An electronic endoscope apparatus, comprising:
a scope and
a processor processing equipment for processing an image obtained by the scope,
the processing equipment including:
a signal processing circuit on a main circuit board;
a dedicated image processing circuit board including a plurality of image processing sections, each for performing a different type of image processing on the image, configured such that ON/OFF of functions thereof and/or processing parameters therefor are set individually with respect to each of the image processing sections; and
a first memory having at least one area configured to store ON/OFF settings of the functions of each of the image processing sections, and/or the values of the processing parameters used by each of the image processing sections; and
a first microcomputer for setting a function of each of the image processing sections to ON or OFF and supplying a predetermined parameter to each of the image processing sections; and
an input device for accepting input from a user, and
the scope including a second memory having at least one area configured to store ON/OFF setting of the function of each of the image processing sections and/or a value of the processing parameter used by each of the image processing sections, wherein
the input device is configured to accept selection input regarding whether to select between a first information, which is information stored in the first memory, and a second information, which is information stored in the second memory, as information to be used in each of the image processing sections; and
the first microcomputer of the processing equipment reads one of the first information and the second information according to a user selection accepted by the input device, from the area of the first memory or the area of the second memory, and performs the setting based on the read out information by connecting the signal processing circuit to the dedicated image processing circuit board only in cases that a connection between the signal processing circuit and the dedicated image processing circuit is judged from the read out information to be necessary.

2. The electronic endoscope apparatus as claimed in claim 1, wherein the processing equipment further comprises:
an input device for accepting input of ON/OFF of the functions and/or the processing parameters individually with respect to each of the image processing sections; and
a second microcomputer configured to store ON/OFF setting of the function and/or the processing parameter specified through the input device with respect to each of the image processing sections in the memory of the scope.

3. The electronic endoscope apparatus as claimed in claim 1, wherein the memory has the area in a plurality.

* * * * *